United States Patent [19]

Rother

[11] Patent Number: 5,113,861
[45] Date of Patent: May 19, 1992

[54] METHOD FOR PROCESSING SIGNALS, PARTICULARLY FOR OXIMETRIC MEASUREMENTS ON LIVING HUMAN TISSUE

[75] Inventor: Peter Rother, Los Altos, Calif.

[73] Assignee: Hewlett-Packard Company, Palo Alto, Calif.

[21] Appl. No.: 340,969

[22] Filed: Apr. 20, 1989

[30] Foreign Application Priority Data

May 9, 1988 [EP] European Pat. Off. ........ 88107438.9

[51] Int. Cl.$^5$ .............................................. A61B 5/00
[52] U.S. Cl. ...................... 128/633; 356/41
[58] Field of Search .................. 364/413.09, 496, 497, 364/498, 499, 525, 571.02, 724.01, 724.13; 128/633, 664, 665, 666; 356/41; 371/6, 64; 328/162, 165, 167

[56] References Cited

U.S. PATENT DOCUMENTS

| | | | |
|---|---|---|---|
| 3,987,293 | 10/1976 | Crooke | 364/825 |
| 4,714,080 | 12/1987 | Edgar, Jr. et al. | 128/633 |
| 4,811,097 | 5/1989 | Ritter et al. | 364/724.01 |

OTHER PUBLICATIONS

Proceedings of the IEEE vol. 64, no. 8, Aug. 1976, New York, USA, pp. 1151-1162.

Primary Examiner—Vincent P. McGraw
Assistant Examiner—LaCharles P. Keesee
Attorney, Agent, or Firm—Richard F. Schuette

[57] ABSTRACT

A method is used for processing signals, particularly for oximetric measurements on living human tissue. Spurious signals are suppressed with respect to information signals. The spurious signals have a frequency lying in a first frequency range, and the information signals have a frequency lying in a second frequency range being different from said first frequency range. The signals are conducted over a filter having essentially a blocking characteristic in said first frequency range and having essentially a transmission characteristic in said second frequency range. An output signal of the filter is further processed.

In order to eliminate distorting effects from the filter on the information signal, a first function is determined representing the deviation of the frequency response of the filter in said frequency range from an ideal transmission characteristic. A second function inverted with respect to said first function is generated. The output signal is weighted by the second function to generate a weighted output signal.

29 Claims, 9 Drawing Sheets

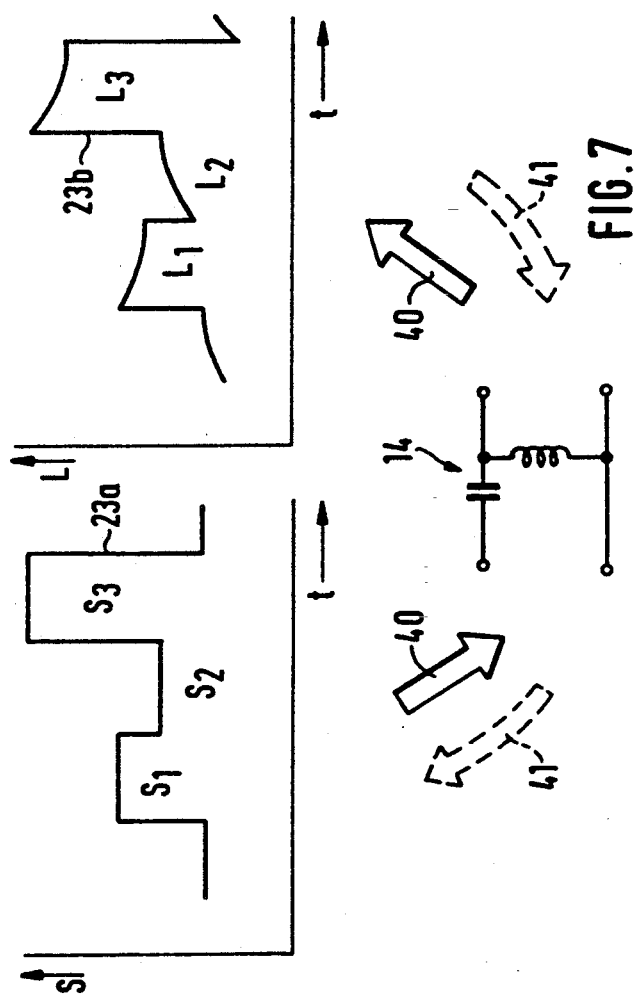

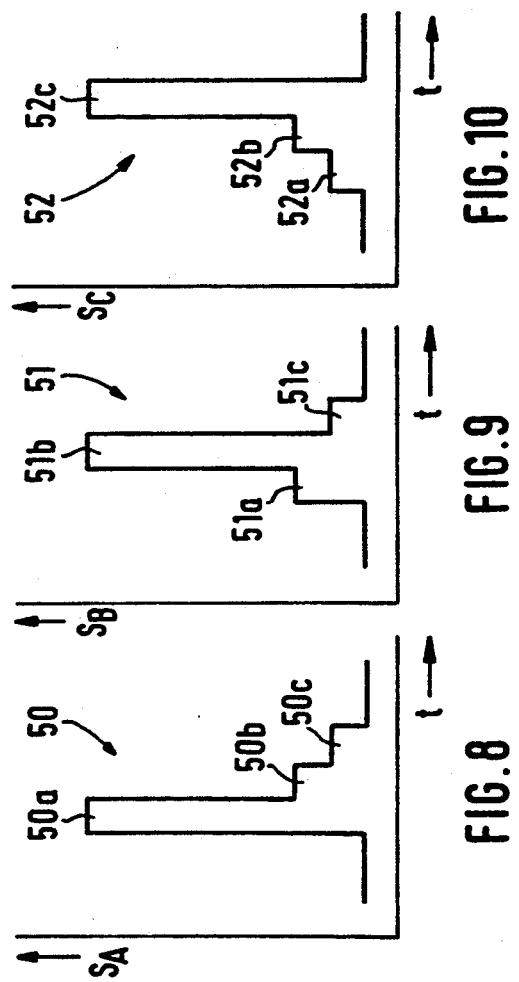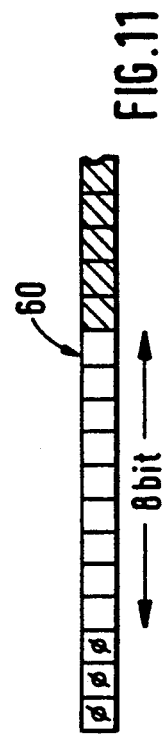

$$S_1 = a_{11}L_1 + a_{12}L_2 + a_{13}L_3$$
$$S_2 = a_{21}L_1 + a_{22}L_2 + a_{23}L_3$$
$$S_3 = a_{31}L_1 + a_{32}L_2 + a_{33}L_3$$
← EQUATION 1

$$\bar{S} = A * \bar{L}$$
← EQUATION 2

$$A = \begin{pmatrix} a_{11} & a_{12} & a_{13} \\ a_{21} & a_{22} & a_{23} \\ a_{31} & a_{32} & a_{33} \end{pmatrix}$$

$$\bar{S} = \begin{pmatrix} S_1 \\ S_2 \\ S_3 \end{pmatrix}$$
← EQUATION 3

FIG 12

$$S_{3\times3} = A_{3\times3} * L_{3\times3}$$

$$\bar{S} = (\bar{S}_A \mid \bar{S}_B \mid \bar{S}_C) = \begin{pmatrix} 14921 & 1233 & 2475 \\ 2469 & 14916 & 1231 \\ 1241 & 2477 & 14929 \end{pmatrix} \quad \text{EQUATION 4}$$

$$\bar{L} = (\bar{L}_A \mid \bar{L}_B \mid \bar{L}_C) = \begin{pmatrix} 14456 & 1504 & 2700 \\ 1499 & 14662 & 1601 \\ 474 & 1723 & 14776 \end{pmatrix} \quad \text{EQUATION 5, EQUATION 6}$$

$$A = \begin{pmatrix} 1.0349 & -.0198 & -.0195 \\ .0668 & 1.0150 & -.0389 \\ .0483 & .0469 & .9962 \end{pmatrix} \quad \text{EQUATION 7}$$

FIG 13

$$A = \begin{pmatrix} \approx & \cdots & \cdots \\ \vdots & \approx & \vdots \\ \cdots & \cdots & \approx \end{pmatrix} \quad \leftarrow \text{EQUATION 8}$$

$$Eps = A - \begin{pmatrix} 1 & 0 & 0 \\ 0 & 1 & 0 \\ 0 & 0 & 1 \end{pmatrix} = A - I \quad \leftarrow \text{EQUATION 9}$$

$$\bar{S} = (I + Eps) * \bar{L} \quad \leftarrow \text{EQUATION 10}$$

$$C = 2^8 * 2^3 * Eps = \begin{pmatrix} 71 & -40 & -40 \\ 137 & 31 & -80 \\ 99 & 96 & -8 \end{pmatrix} \quad \leftarrow \text{EQUATION 11}$$

FIG 14

$$A^* = \begin{pmatrix} a_{11}/a_{11} & a_{12}/a_{11} & a_{13}/a_{11} \\ a_{21}/a_{22} & a_{22}/a_{22} & a_{23}/a_{22} \\ a_{31}/a_{33} & a_{32}/a_{33} & a_{33}/a_{33} \end{pmatrix} = \begin{pmatrix} 1 & -.0191 & -.0188 \\ .0658 & 1 & -.0389 \\ .0485 & .0471 & 1 \end{pmatrix} \leftarrow \text{EQUATION 12}$$

$$C^* = \begin{pmatrix} 0 & -39 & -39 \\ 135 & 0 & -80 \\ 99 & 96 & 0 \end{pmatrix} \leftarrow \text{EQUATION 13}$$

FIG 15

$$S_1 = L_1 + a^*_{12}L_2 + a^*_{13}L_3 = L_1 - (C^*_{12}L_2 + C^*_{13}L_3)/256 \cdot 8$$
$$S_2 = L_2 + a^*_{21}L_1 + a^*_{23}L_3 = L_2 + (C^*_{21}L_1 - C^*_{23}L_3)/256 \cdot 8$$
$$S_3 = L_3 + a^*_{31}L_1 + a^*_{32}L_2 = L_3 + (C^*_{31}L_1 + C^*_{32}L_2)/256 \cdot 8 \quad \leftarrow \text{EQUATION 14}$$

$$COR_1 + S_1 = (L_1 + H) + a^*_{12}(L_2 + H) + a^*_{13}(L_3 + H)$$
$$COR_2 + S_2 = (L_1 + H) + a^*_{21}(L_2 + H) + a^*_{23}(L_3 + H)$$
$$COR_3 + S_3 = (L_1 + H) + a^*_{31}(L_2 + H) + a^*_{32}(L_3 + H) \quad \leftarrow \text{EQUATION 15}$$

$$S_1 = L_1 = L_2 = L_3 = 0 \quad \leftarrow \text{EQUATION 16}$$

$$COR_1 = (\;1\; + a^*_{12} + a^*_{13})H$$
$$COR_2 = (a^*_{21} + \;1\; + a^*_{23})H$$
$$COR_3 = (a^*_{31} + a^*_{32} + \;1\;)H \quad \leftarrow \text{EQUATION 17}$$

$$S_1 = L'_1 - C^*_{12}L'_2/2^{11} - C^*_{13}L'_3/2^{11} - COR_1$$
$$S_2 = L'_2 + C^*_{21}L'_1/2^{11} - C^*_{23}L'_3/2^{11} - COR_2$$
$$S_3 = L'_3 + C^*_{31}L'_1/2^{11} + C^*_{32}L'_2/2^{11} - COR_3 \quad \leftarrow \text{EQUATION 18}$$

FIG 16

METHOD FOR PROCESSING SIGNALS, PARTICULARLY FOR OXIMETRIC MEASUREMENTS ON LIVING HUMAN TISSUE

BACKGROUND OF THE INVENTION

The invention relates to a method for processing signals, particularly for oximetric measurements on living human tissue, in which spurious signals are suppressed with respect to information signals, said spurious signals having a frequency lying in a first frequency range and said information signals having a frequency lying in a second frequency range being different from said first frequency range, said signals being conducted over a filter having essentially a blocking characteristic in said first frequency range and having essentially a transmission characteristic in said second frequency range, an output signal of said filter being further processed.

It is well-known in the art to perform measurements of various physical quantities by using detectors, to convert the physical quantity into electric voltages. However, when processing the electrical signal, derived from such detectors, one has to take into account that the information signals, i.e. the signals, representing the desired physical quantities, are mostly superimposed by spurious signals coming from various sources. The effect of spurious signals becomes more important, the more the sensitivity of the measuring circuitry is enhanced. Typical examples for spurious signals are drift signals, i.e. low-frequency aberrations being generated by thermal effects, by slow alterations of supplying voltages, etc.

When the frequency of such spurious signals is different from the frequency of the information signals, one can easily suppress the spurious signals by inserting filter circuits into the measuring circuitry which have a blocking characteristic in the frequency range of the spurious signals and which have a transmission characteristic in the frequency range of the information signals.

In the field of oximetric measurements on living human tissue, it is known to use photoelectric probe heads exhibiting a plurality of light-emitting elements, e.g. light-emitting diodes (LED) which are tuned to different wavelengths so that light beams of different wavelength may be emitted on the human tissue under investigation. The light beams, having penetrated the tissue, are then directed on a photo-sensitive device which converts the impinging light beams into electrical signals.

However, when performing such measurements, one potential source of spurious signals is the ambient light at the location where the measurement is performed. Considering that human tissue is partially transparent to light, it can easily be understood that the photo-sensitive device used in oximetric measurements is not only subject to the light beams, generated by the light-emitting elements but also to ambient light, be it generated by electric lamps or be it natural day-light. Ambient light may vary in amplitude during the time where the measurement is performed so that the photo-sensitive device will detect a mixture of slowly varying ambient light and of the light beams generated by the light-emitting elements.

In order to overcome these deficiencies, it is well-known in the art to use multiplex techniques. For this purpose, pulse trains are generated, being composed by individual pulses, each of which being generated by a light-emitting element and, thus, corresponding to a light beam of different wavelength. One can, for example, use pulse trains having three individual pulses corresponding to short light pulses of three different wavelengths. One can, further, timely separate the pulse trains by a short break, during which no light is emitted so that the electrical signal, generated by the photo-sensitive device during such break, is only dependent on ambient light.

As long as the influence of ambient light is constant, one can easily measure an offset-value corresponding to the electrical signal during the break and can subtract the offset-value from any succeeding electrical signals received when the pulse trains appear. Such offset-compensation is, however, only effective if the influence of ambient light is constant within the desired precision of measurement.

However, in most cases, this is not true, because the influence of ambient light varies with time and can, therefore, not be compensated by simply subtraction measures.

Therefore, one has tried to overcome these problems by inserting appropriate filter circuitry into the signal path behind the photo-sensitive element. Considering that the pulse frequency is relatively high, i.e. in the order of magnitude of several hundred cps, and considering, further, that the variation of ambient light is in the order of a few cps, one has used high-pass filter circuits to suppress spurious signals generated by the variation of ambient light.

However, due to the fact that all filters have a frequency characteristic influencing frequency bands lying octaves away, inserting a high-pass filter into the signal path of an oximetric measuring instrument would result in a distortion of the information signal even if the frequency of the information signals is several orders of magnitude away from the spurious signal frequency. This holds true the more the sensitivity of the oximetric system shall be enhanced which requires a high-precision of amplitude measurement on the light pulses received by the photo-sensitive element.

It is, therefore, an object of the present invention to improve the method mentioned above by effectively suppressing spurious signals and, concurrently, preserving the precision of high-sensitivity measurements.

BRIEF DESCRIPTION OF THE INVENTION

This object is achieved according to the invention by determining a first function representing the deviation of the frequency response of said filter in said second frequency range from an ideal transmission characteristic, generating a second function inverted with respect to said first function and weighting said output signal by said second function to generate a weighted output signal.

The object of the invention is, thus, fully achieved, because all distortions, generated by the filter, are fully eliminated, since the signal, appearing at the output of the filter, is electrically processed exactly the opposite way as was the case in the filter with respect to the distorting characteristic from the spurious signal frequency range still being effective in the information frequency range.

Therefore, irrespective of what these distortional effects are and how effective they may be, these distorting effects are fully compensated for by using an inverted characteristic and applying such characteristic on the signal at the output of the filter.

In a preferred embodiment of the invention, the information signal is a multiplexed signal having pulse trains of a high frequency, said spurious signals having a low frequency, and said filter being a high-pass filter.

As explained above, this embodiment of the invention can advantageously be used for all measurements where spurious signals appear in the low-frequency range, as is the case with thermal variations, long-term variations of supply voltages and, above all, in the case of measurements using light beams in the presence of varying ambient light.

In another preferred embodiment of the invention, the inverted function is a first square matrix having a number of lines and columns being equal to the number of pulses of said pulse trains, said output signal being represented as a second square matrix of amplitudes of pulses of pulse trains appearing at the output of said high-pass filter, said first and second matrices being multiplied by each other to generate a third square matrix of amplitudes of pulses of pulse trains of said weighted output signal.

This embodiment of the invention is particularly advantageous, because one can easily perform matrix operations by using digital electronics to convert incoming signals into weighted output signals. Once the first function representing the deviation of the frequency response of the filter in the second frequency range is known, one can easily convert the first function into a matrix, store such matrix in an electronic memory and performing weighting operations on the incoming measuring signal by transforming the pulse train signals into a matrix and multiplying this matrix with the one matrix stored in the memory.

According to another preferred embodiment of the invention, one can determine coefficients of said first matrix in that a number of test pulse trains of a predetermined first amplitude is fed to said high-pass filter, said number of test pulse trains as well as the number of test pulses of each of said test pulse trains corresponding to said number of lines and columns of said first matrix, second amplitudes of pulses appearing at said output of said high-pass filter in response to said test pulses being measured, and said coefficients being determined by dividing a fourth matrix defined from said first amplitudes by a fifth matrix defined from said second amplitudes.

This embodiment of the invention has the particular advantage of allowing to determine the first function representing the deviation of the frequence response of the filter in the second frequency range by once testing the filter with test pulse trains of known amplitudes. When applying the test pulse trains on the filter in the absence of any spurious effects, one can, thus, determine the characteristic of the filter as a matrix of coefficients in order to then perform the afore-explained operations on incoming measuring signals during actual measurements.

According to a further preferred embodiment of the invention, the test pulse trains exhibit each one pulse having a high first amplitude, the other pulses having low first amplitudes.

When doing so, one can enhance the precision of succeeding matrix calculations and one can obtain matrices of diagonal form which, further, enhance the precision of measurements and reduce the expenditures of weighting operations.

According to a further embodiment of the invention, one can decrease the principal diagonal coefficients of said first matrix by unity, factor out the value of a n-th power of two, and digitally multiply said second matrix by said first matrix using digital words having a number of bits smaller than n.

These measures allow to reduce the amount of operations on the measured signal. If, e.g., the matrix coefficients are processed with a precision of 16 bits, the multiplication of matrices would require nine multiplying operations in $16 \times 16$ bit technology or thirty six operations in $8 \times 8$ bit technology, respectively. However, when proceeding according to the afore-mentioned embodiment of the invention, one can reduce these operations to one half, i.e. to nine operations in $8 \times 16$ bit technology or eighteen operations in $8 \times 8$ bit technology. In practical examples, one has found that in spite of this drastic reduction in operations, the residual error is negligible, because it is smaller than $10^{-3}$.

According to another embodiment of the invention, one can, alternately, standardize the principal diagonal coefficients of said first matrix on unity, then, again, factor out the value of a n-th power of two, and digitally multiply said second matrix by said first matrix using digital words having a number of bits smaller than n.

This embodiment of the invention, too, has the particular advantage of reducing the number and extent of operations, necessary to process the signal from the output of the high-pass filter. Making again reference to the above-mentioned example with the necessity of performing nine multiplications in $16 \times 16$ bit technology without the particular measures of the embodiment of the invention, one can achieve a reduction to six operations in $8 \times 16$ bit technology or twelve operations in $8 \times 8$ bit technology, respectively.

According to a further embodiment of the invention, one can weight an offset-value by said first matrix, having its principal diagonal coefficients standardized to unity to generate a sixth matrix of correction values, said correction values being subtracted from said weighted signals generated from pulse trains exhibiting said offset-value.

This embodiment of the invention has the particular advantage of avoiding bipolar operations. If the offset-value of constant amplitude were compensated for at the input of the high-pass filter, the distortion, generated by the high-pass filter, could result in negative polarities of output signals which, again, would generate the necessity of performing bipolar operations on the output signal of the high-pass filter. In contrast, the afore-mentioned measures of this particular embodiment of the invention allows to compensate for constant offset-values at the output of the high-pass filter by introducing a correction operation in which the constant offset-value, too, is weighted by the transmission characteristic of the high-pass filter.

Although the present invention may be applied in various fields of measuring technology, it is particularly preferred to use the invention in the field of oximetric measurements on living human tissue. In that case, one preferably uses a plurality of light-emitting elements sending in timely spaced relationship first pulsed light beams of different wavelength on a living human tissue supplied with blood, second light beams having passed said tissue being guided on a light-receiving element, said light-receiving element generating said multiplexed signal.

Thus, the invention allows to use all of the aforementioned advantages in connection with oximetric measurements so that the oxygen saturation of blood may be measured on a patient with unparalleled precision, because one can effectively eliminate all measuring errors generated by spurious signals, particularly by slowly varying ambient light.

Further advantages of the invention will become apparent from the description of embodiments as well as from the accompanying drawings. It goes, further, without saying that all of the afore-mentioned elements may be used separately or in other combinations as expressedly mentioned without deviating from the scope of the present invention.

BRIEF DESCRIPTION OF THE DRAWINGS

In the following description of embodiments, the invention is illustrated by means of the drawings, in which

FIG. 7 is a schematic representation of a pulse train signal as affected when being guided over a high-pass filter;

FIGS. 8 through 10 show test pulse trains as used for determining the transmission characteristics of a high-pass filter according to the invention;

FIG. 11 shows a schematic representation of a memory cell in which a digital word is stored.

FIGS. 12-16 further illustrate various formula (1) through (18) and are further explained in the following description of embodiments.

DETAILED DESCRIPTION OF THE INVENTION

As already explained hereinbefore, the present invention may be used for a wide range of measuring problems. However, for the sake of clarity, the following description of embodiments makes reference to oximetric measurements on human tissue supplied with blood.

Oximetric measurements of this kind are performed in order to determine the saturation of oxygen within the blood of a patient. It is well-known in the art to evaluate the oxygen supply in the circulation of a patient by determining the amount of the patient's hemoglobin, carrying chemically bound oxygen molecules compared to the amount of the total patient hemoglobin as a percentage.

Common techniques use light beams emitted on patient's tissue, e.g. on the finger of a patient, where the light beam penetrates a part of the patient's tissue either in a transmission or a reflection mode. By measuring the light absorption for various wavelengths in the visible and the infrared range, one can calculate transmission or reflection characteristics and, thus, determine the oxygen saturation.

Figure 1:
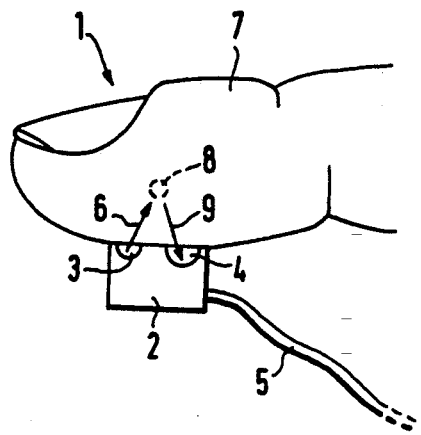
FIG. 1 shows a measuring detector applied to a finger of a patient for performing oximetric measurements of the finger tissue.

Referring now to FIG. 1, 1 designates a finger of a patient under investigation. A pick-up 2 is provided with a plurality of light-emitting elements 3, one of which being shown in FIG. 1 by means of example. The light-emitting elements 3 can be made as light-emitting diodes or any other comparable elements, capable of emitting light within the visible and the infrared range. The elements 3 are designed such to emit light of different wavelengths.

The pick-up 2 is, further, provided with one or more light-receiving elements 4, e.g. a photo-sensitive transistor.

A cable 5 is provided for feeding both the light-emitting elements 3 as well as the light-receiving element or elements 4 with electrical energy and for feeding signals to and from the pick-up 2.

When the pick-up 2 is pressed to the patient's finger 1 and appropriate control signals are fed to the pick-up 2 via cable 5, first beams of light 6 are emitted on the patient's tissue, designated by reference numeral 7. The hemoglobin in the patient's tissue 7 is shown at 8. When the first light beams 6 impinge on hemoglobin 8, a second beam of light is reflected onto light-receiving element or elements 4. An appropriate electrical signal is then generated and transmitted via cable 5 to an electronic circuitry, not shown in FIG. 1.

According to the amount of hemoglobin 8, being chemically bound to oxygen molecules or not, the first beams of light 6 are more or less absorbed by hemoglobin 8 and, thus, the second beams of light 9 vary in amplitude depending on the amount of oxygen saturation of hemoglobin 8 and, further, depending on the particular wavelength used.

Figure 2:
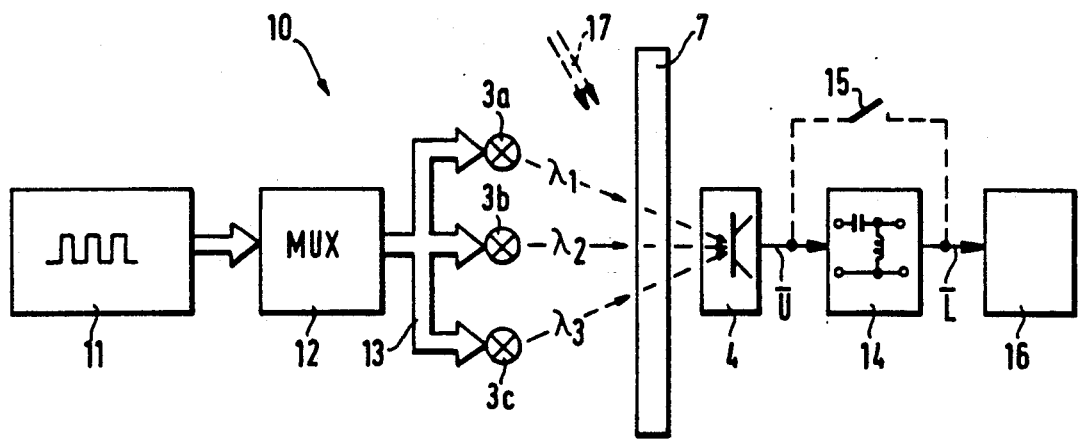
FIG. 2 is a schematic block diagram of an oximetric measuring instrument.

FIG. 2 shows a block diagram of an oximetric measuring circuit, indicated as a whole at 10. 11 designates a pulse generator, delivering control pulses to a multiplexer 12. The multiplexer 12 is used to generate pulse patterns in order to activate light-emitting elements $3a$, $3b$, and $3c$, respectively. The wavelength of the light beams, emitted by light-emitting elements $3a$, $3b$, and $3c$ are designated by $\lambda_1$, $\lambda_2$ and $\lambda_3$, respectively.

After having passed through the patient's tissue, schematically designated at 7 in FIG. 2, the light beams impinge on light-receiving element 4, being represented as a photo-sensitive transistor in FIG. 2. The output signal of light-receiving element 4 is designated as $\overline{U}$.

Voltage U is then fed to a high-pass filter 14, the output signal of which is designated by L. In a specific mode of operation, high-pass filter 14 may be bypassed by closing a switch 15, as will be explained below. Output signal L is then fed to an evaluation circuit, indicated at 16.

The purpose of circuitry 10 of FIG. 2 is to generate light pulses by activating light-emitting elements $3a$, $3b$, and $3c$, respectively, in timely spaced relationship, i.e. by activating the said elements one after the other. Thus, pulse trains of light beams with varying amplitude and varying wavelength are generated and received in light-receiving element 4 after having passed through tissue 7. However, when performing such measurements, light-receiving element 4 is, further, subjected to ambient light, schematically indicated at 17. Thus, output signal U is a mixture of information signals, i.e. absorption response of tissue 7 with respect to the light pulses emitted from light-emitting elements 3a through 3c and spurious signals as generated by ambient light 17. The purpose of high-pass filter 14 and evaluation circuit 16 in combination with switch 15 is to eliminate any error signals generated by ambient light 17, as will now be described in further detail.

Figure 3:
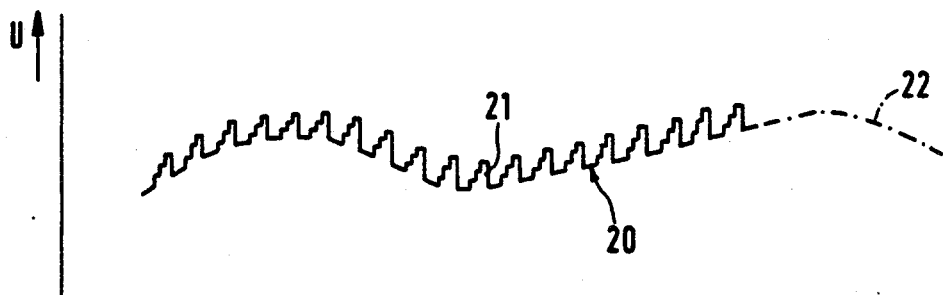
FIG. 3 is a schematic representation of a signal voltage vs. time appearing at the output of a photo-sensitive element as used in the block diagram of FIG. 2.

FIG. 3 shows a voltage vs. time characteristic of a signal 20 as appearing at the output of light-receiving element 4. As can easily be seen from FIG. 3, signal 20 is a mixture of an information signal 21 shaped as pulse trains and a spurious signal 22 having the shape of a slowly varying background signal.

Figure 4:
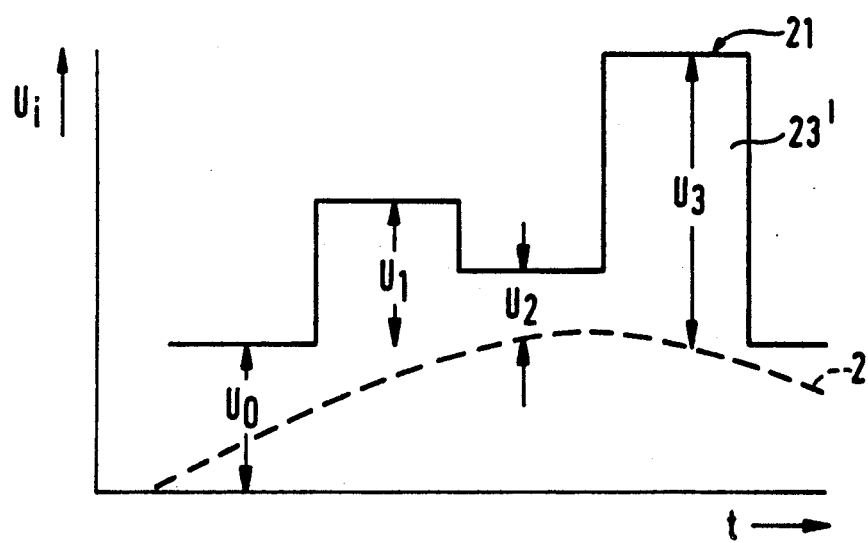
FIG. 4 is a voltage vs. time diagram corresponding to an information signal and a spurious signal, respectively.

Referring now to FIG. 4, one can see the information signal 21 in a somewhat larger scale. Information signal 21 consists of a pulse train 23' in which a break is followed by three pulses having voltage amplitudes of $U_1$, $U_2$, and $U_3$, respectively. In the break preceding the three pulses, an offset-value $U_0$ is measurement, and the subsequent voltage amplitudes $U_1$, $U_2$, and $U_3$ are measured with respect to offset-value $U_0$.

Pulse train 23' of FIG. 4 would represent an ideal signal in the absence of spurious signal 22.

Figure 5:
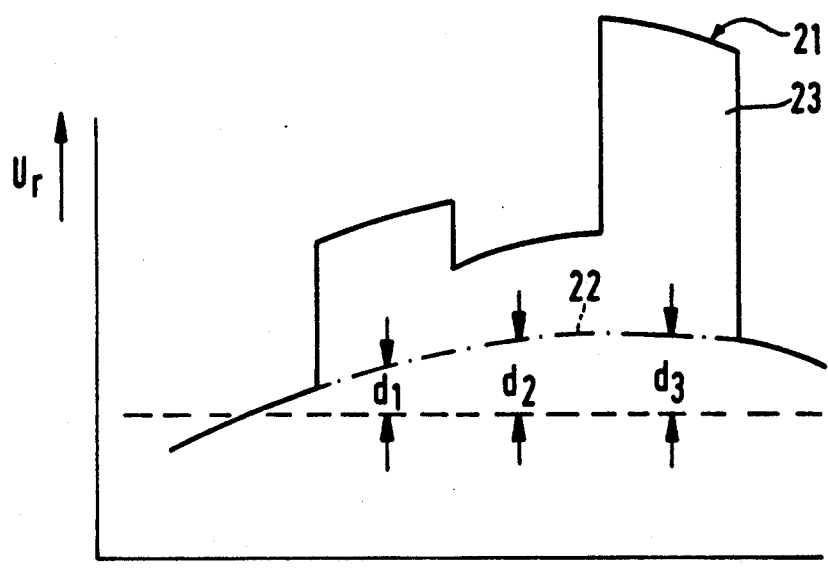
FIG. 5 is a diagram, similar to that of FIG. 4, showing the resulting signal in which the information signal and the spurious signal are mixed.

However, when considering the mixture of the two afore-mentioned signals, one would come to a representation as shown in FIG. 5 where 23 indicates a real pulse train as actually measured in the presence of spurious signal 22.

As can easily be seen from FIG. 5, pulse train 23 is distorted with respect to the ideal pulse train 23' of FIG. 4 in that deviation signals $d_1$, $d_2$, and $d_3$ must be taken into account when measuring the actual voltage amplitude of the pulses of pulse train 23. If spurious signal 22 has a stochastic amplitude vs. time characteristic, it is not possible to eliminate deviation values $d_1$ through $d_3$ by using extrapolation techniques.

However, considering that in the case of low-frequency spurious signals the frequency range of the spurious signals is orders of magnitude lower than the frequency range of the information signals, one can use a frequency band separation technique.

Figure 6:
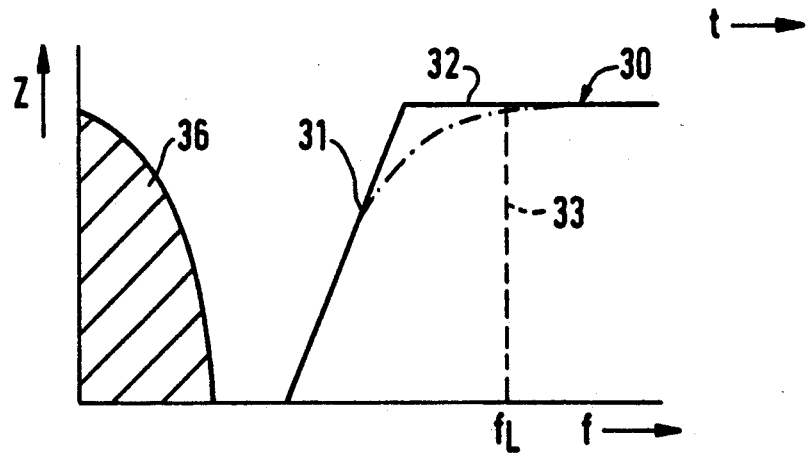
FIG. 6 is a transmission coefficient vs. frequency diagram showing the frequency range of spurious signals as become effective in oximetric measurements as well as a characteristic of a high-pass filter.

FIG. 6 is a transmission factor vs. frequency diagram in which 30 represents a high-pass filter characteristic. 31 designates the filter attenuation in the blocking band whereas 32 designates the filter transmission in the transmission band. 33 indicates frequency $f_L$ of the pulses used for pulse trains 23.

In contrast, 36 designates the spectral distribution of spurious signals as occurring during oximetric measurements in the presence of ambient light. As one can clearly see from FIG. 6, the frequency range of the spurious signals is different from the frequency range of transmission band 32 of high-pass filter 14. In a practical example, spurious signals occur in a frequency band below 5 cps whereas frequency $f_L$ of pulse trains 23 may be set to be 400 cps up to several thousand cps.

However, in practice a strict separation between blocking band and transmission band of a high-pass filter cannot be achieved. As a result, the attenuating behaviour of a high-pass filter in its blocking range becomes also effective in its transmission band, as indicated by a dash-dot-line in FIG. 6.

The result of such practical behaviour of high-pass filters is depicted in FIG. 7.

The left upper corner of FIG. 7 shows an ideal pulse train 23a composed of pulse signals $S_1$, $S_2$, and $S_3$. When pulse train 23a is subjected to high-pass filter 14, as indicated by arrow 40 in FIG. 7, an output signal L is generated having the shape of pulse train 23b in the right upper corner of FIG. 7 with pulse signals $L_1$, $L_2$, and $L_3$, respectively.

The conversion of pulse train 23a into pulse train 23b corresponds to the frequency response of high-pass filter 14. In other words, if the conversion characteristic of high-pass filter 14 is known, one can re-convert pulse train 23b by electronic manipulation as indicated by arrows 41 in FIG. 7 in order to re-transform distorted pulse train 23b into ideal pulse train 23a.

In order to do so, one can write down the conversion of distorted pulse train 23b into ideal pulse train 23a as a system of equations (1) in which signals $S_1$, $S_2$, and $S_3$ are calculated from pulse signals $L_1$, $L_2$, and $L_3$, respectively, by using coefficients $a_{ik}$. In other words, a matrix of signals S may be determined by multiplying a matrix of signals L by a matrix A according to equation (2) where matrix A is written down with its coefficients $a_{ik}$.

Thus, ideal signals S may be determined as a matrix S as shown in equation (3).

In order to perform the conversion as explained before, one has first to determine matrix A according to equation (2).

In order to do so, one can use a technique in which test pulse trains are applied to the input of high-pass filter 14 in the FIG. 2 circuit in two operational modes, the first of which having switch 15 open and the second of which having switch 15 closed.

To do so, test pulse trains may be used as shown in FIGS. 8 through 10.

A first test pulse train 50 as shown in FIG. 8 has a first pulse 50a of a high amplitude succeeded by two further pulse trains 50b and 50c of lower but different amplitudes, respectively. A second test pulse train as shown in FIG. 9 has a first low-amplitude pulse 51a, a second high-amplitude pulse 51b, and a third low-amplitude pulse 51c. Finally, a third test pulse train as shown in FIG. 10 has a first low-amplitude pulse 52a, a second low-amplitude pulse 52b, and a third high-amplitude pulse 52c.

The reason for using test pulse trains 50 through 52 with one high-amplitude pulse and two low-amplitude pulses each, is to enhance the precision in the determination of matrix A.

Having performed the afore-mentioned operations, one has three matrix equations in which the undistorted signal (switch 15 closed) is depending on the distorted signal (switch 15 opened).

This matrix equation system as written down in equation (4) may be reduced to one S-matrix and one L-matrix as written down in equations (5) and (6), respectively. In equations (5) and (6), respectively, numerical values are given as an example for one practical application where a standard commercial oximetric measuring system SaO₂-Clover D of the applicant was used in connection with a second order high-pass filter having a cut-off frequency of 30 cps. The S-matrix numerical values were achieved with the high-pass filter 14 bypassed whereas the L-matrix numerical values were measured with the high-pass filter inserted into the circuitry.

The A-matrix may be determined from the S- and the L-matrix, respectively, by dividing the S-matrix by the L-matrix. Considering the numerical values as written down in equations (5) and (6), respectively, one comes to the numerical values for the A-matrix as written down in equation (7).

As one can easily see from equation (7), this matrix is to a high degree diagonal, because its principal diagonal coefficients $a_{11}$, $a_{22}$, $a_{33}$, respectively, are almost exactly equal to unity. This is because in view of the great distance between the respective frequency bands of the spurious signals and the information signals, the amplitudes of distorted signals L are at a first glance equal to the amplitudes of undistorted signals S.

In a practical test, one has applied the A-matrix according to equation (7) to operational pulse trains of the oximetric system used and has found that the accuracy of the coefficients as written down in equation (7) is better than $10^{-3}$ and, thus, is below the noise level of the particular system used.

When performing matrix division on the values as written down in equations (5) and (6), respectively, one has to perform nine multiplications in 16×16 bit technology considering that the principal diagonal coefficients of equations (5) and (6) have five decimal digits.

In order to reduce the necessary operations, one may recall that the A-matrix of equation (7) is highly diagonal as again represented in equation (8) where the principal diagonal coefficients are said to be unity and all coefficients of the upper half are negative and all coefficients of the lower half are positive.

In view of the symmetry of the A-matrix, one can make a modification on this matrix by creating a modified matrix Eps as written down in equation (9). Matrix Eps is determined by subtracting a unity matrix from matrix A.

The signal matrix S may now be written as equation (10) by combining equations (1) and (9).

Factoring now out powers of two, namely $2^8$ and $2^3$, one can write a one-Byte coefficient matrix C as shown in equation (11). As a result, the coefficients used for the necessary matrix division as explained above with respect to equations (5) through (7) are reduced to one-Byte coefficients having a maximum of three decimal digits, as can be seen in equation (11).

FIG. 11 shows a digital word 60 in schematic representation as forming part of a digital memory or a central processing unit (CPU) of a microcomputer signal processing unit.

As one can see from FIG. 11, one can easily incorporate an 8-bit word into a 16-bit memory by placing the 8-bit word (one Byte) into memory positions "5" through "12", leaving positions 0 through 4 blank and inserting zero values into positions "13" through "15". Thus, a $\pm 2^{-12}$ precision may be achieved.

Thus, all coefficients may be stored in one Byte (8-bit) with a precision of $\pm 2^{-12}$ or 0,25%, respectively. Thus, instead of making nine multiplications in 16×16 bit technology or thirty six multiplications in 8×8 bit MUL technology, as explained above, it would be sufficient to make nine multiplications in 8×16 bit technology or eighteen multiplications in 8×8 MUL 8-bit technology, respectively.

A further reduction in the amount of operations may be achieved by standardizing the principal diagonal coefficients $a_{11}$, $a_{22}$, and $a_{33}$, respectively, to unity. This may be achieved by dividing the respective lines of the A-matrix by $a_{11}$, $a_{22}$, and $a_{33}$, respectively, as written down in equation (12).

When using the same steps as explained above with respect to equation (11), one can obtain a modified 8-bit matrix C. as written down in equation (13). As one can easily see by comparing equations (11) and (13), the principal diagonal elements of 8-bit matrix C* are now all zero which again reduces the amount of operations to six multiplications in 8×16 bit technology or twelve multiplications in 8×8 MUL 8-bit technology, respectively.

This can easily be acknowledged when writing down the respective equations for signals $S_1$, $S_2$, and $S_3$, respectively, as can be seen in equation (14). In equation (14), signals $S_1$, $S_2$, and $S_3$ are determined from amplitudes $L_1$, $L_2$, and $L_3$ by various multiplication and addition/subtraction operations with various coefficients of the A* and C* matrix as written down in equations (12) and (13), respectively.

Another aspect of the present invention is to further eliminate offset of pulse amplitudes appearing at the output of light-receiving device 4 which may not be generated by ambient effects but rather by light-receiving elements for themselves.

In principle, one could subtract an appropriate offset-value from the signals appearing at the output of light-receiving elements 4 which, however, could result in negative polarity signals at the output of high-pass filter 4 considering e.g. signals L of FIG. 7 exhibiting undershoot effects at trailing edges of pulses $L_1$, $L_2$ and $L_3$, respectively.

In order to avoid bipolar operations in evaluation circuit 16, one can introduce correction values $COR_1$, $COR_2$, and $COR_3$, respectively, as written down in equation (15).

Equations (15) are derived under the assumption that a constant offset-value H appears at the output of light-receiving elements 4 and using a signal processing as explained above with respect to equations (12) and (13), respectively.

Under the assumption of equation (16), one can write a correction value matrix COR as written down in equation (17) where correction values $COR_1$, $COR_2$, and $COR_3$, respectively, may be calculated from constant offset-value H by using the $a_{ik}^*$ coefficients of the modified A* matrix of equation (12).

Combining equations (14) and (17), one comes to equation (18) showing ideal signals $S_1$, $S_2$, and $S_3$, respectively, as calculated from distorted signals $L_1'$, $L_2'$, and $L_3'$ respectively, where the apostrophe was added to indicate that distorted signals $L_1'$, $L_2'$, and $L_3'$ were measured in the presence of a constant value offset H.

Thus, additional offset-effects may be compensated for as generated, e.g., by the light-receiving elements 4 without the necessity of introducing bipolar operations during further signal processing in evaluation circuit 16.

I claim:

1. A method for deriving output signals from spurious signals having a frequency lying in a first frequency range and n multiplexed information signals having a frequency lying in a second frequency range that is different from said first frequency range, said method comprising the steps of:

passing said signals through a filter having an essentially blocking characteristic in said first frequency range and having an essentially transmitting characteristic in said second frequency range so as to produce a column matrix;

providing a first $n^2$ matrix function representing the deviation of the frequency range from an ideal transmission characteristic;

deriving a second $n^2$ matrix function inverted with respect to said first matrix function; and multiplying said column matrix at the output of said filter with said second $n^2$ matrix function to generate said output signals.

2. The method of claim 1 further comprising the step of providing said information signal in the form of a multiplexed signal having pulse trains of a pulse frequency that is above the frequency of said spurious signals.

3. The method of claim 2, wherein said inverted function is a first square matrix having a number of lines and columns, each of which is equal to the number of pulses in a pulse train and wherein said signal passed by said filter is represented as a second square matrix of the respective first amplitudes of pulses of pulse trains appearing at the output of said filter, the step of multiplying said first and second matrices by each other to generate a third square matrix of amplitudes of pulses of pulse trains to produce said output signals.

4. The method of claim 3 further comprising the steps of:
   determining coefficients of said first square matrix by providing a number of test pulse trains of a predetermined fist amplitude to said filter, the number of test pulse trains and the number of test pulses in each of said test pulse trains corresponding to said number of lines and columns of said first square matrix,
   deriving second amplitudes of pulses appearing at the output of said filter in response to said test pulses, and
   dividing a fourth matrix defined from said first amplitudes by a fifth matrix defined from said second amplitudes.

5. The method of claim 4 further comprising the step of providing said test pulse trains in such manner that each train has one pulse having a higher amplitude than the other pulses of said train.

6. The method of claim 3 further comprising the steps of:
   decreasing the principal diagonal coefficients of said first matrix by unity.
   factoring out the value of a n-th power of two, and
   digitally multiplying said second matrix by said first matrix using digital words having a number of bits smaller than n.

7. The method of claim 4 further comprising the steps of:
   decreasing the principal diagonal coefficients of said first matrix by unity,
   factoring out the value of a n-th power of two, and
   digitally multiplying said second matrix by said first matrix using digital words having a number of bits smaller than n.

8. The method of claim 5 further comprising the steps of:
   decreasing the principal diagonal coefficients of said first matrix by unity,
   factoring out the value of a n-th power of two, and
   digitally multiplying said second matrix by said first matrix using digital words having a number of bits smaller than n.

9. The method of claim 3 further comprising the steps of:
   standardizing the principal diagonal coefficients of said first matrix on unity,
   factoring out the value of n-th power of two, and
   digitally multiplying said second matrix by said first matrix using digital words having a number of bits smaller than n.

10. The method of claim 4 further comprising the steps of:
    standardizing the principal diagonal coefficients of said first matrix on unity,
    factoring out the value of n-th power of two, and
    digitally multiplying said second matrix by said first matrix using digital words having a number of bits smaller than n.

11. The method of claim 5 further comprising the steps of:
    standardizing the principal diagonal coefficients of said first matrix on unity,
    factoring out the value of n-th power of two, and
    digitally multiplying said second matrix by said first matrix using digital words having a number of bits smaller than n.

12. The method of claim 9 further comprising:
    weighting an offset-value by said first matrix having its principal diagonal coefficients standardized to unity to generate a sixth matrix of correction values, said correction values being subtracted from said weighted signals generated from pulse trains exhibiting said offset-value.

13. The method of claim 10, further comprising:
    weighting an offset-value by said first matrix having its principal diagonal coefficients standardized to unity to generate a sixth matrix of correction values, said correction values being subtracted from said weighted signals generated from pulse trains exhibiting said offset-value.

14. The method of claim 11, further comprising:
    weighting an offset-value by said first matrix having its principal diagonal coefficients standardized to unity to generate a sixth matrix of correction values, said correction values being subtracted from said weighted signals generated from pulse trains exhibiting said offset-value.

15. The method of claim 2, further comprising the steps of:
    using a plurality of light-emitting elements to send in timely spaced relationship first pulsed light beams of different wavelength into a living human tissue supplied with blood, and
    directing second light beams that have passed through said tissue on to a light-receiving element so as to generate said multiplexed signal.

16. The method of claim 3, further comprising the steps of:
    using a plurality of light-emitting elements to send in timely spaced relationship first pulsed light beams of different wavelength into a living human tissue supplied with blood, and
    directing second light beams that have passed through said tissue on to a light-receiving element so as to generate said multiplexed signal.

17. The method of claim 4, further comprising the steps of:
    using a plurality of light-emitting elements to send in timely spaced relationship first pulsed light beams of different wavelength into a living human tissue supplied with blood, and
    directing second light beams that have passed through said tissue on to a light-receiving element so as to generate said multiplexed signal.

18. The method of claim 5, further comprising the steps of:
    using a plurality of light-emitting elements to send in timely spaced relationship first pulsed light beams of different wavelength into a living human tissue supplied with blood, and directing second light beams that have passed through said tissue on to a light-receiving element so as to generate said multiplexed signal.

19. The method of claim 6, further comprising the steps of:

using a plurality of light-emitting elements to send in timely spaced relationship first pulsed light beams of different wavelength into a living human tissue supplied with blood, and directing second light beams that have passed through said tissue on to a light-receiving element so as to generate said multiplexed signal.

20. The method of claim 7, further comprising the steps of:

using a plurality of light-emitting elements to send in timely spaced relationship first pulsed light beams of different wavelength into a living human tissue supplied with blood, and directing second light beams that have passed through said tissue on to a light-receiving element so as to generate said multiplexed signal.

21. The method of claim 8, further comprising the steps of:

using a plurality of light-emitting elements to send in timely spaced relationship first pulsed light beams of different wavelength into a living human tissue supplied with blood, and directing second light beams that have passed through said tissue on to a light-receiving element so as to generate said multiplexed signal.

22. The method of claim 9, further comprising the steps of:

using a plurality of light-emitting elements to send in timely spaced relationship first pulsed light beams of different wavelength into a living human tissue supplied with blood, and directing second light beams that have passed through said tissue on to a light-receiving element so as to generate said multiplexed signal.

23. The method of claim 10, further comprising the steps of:

using a plurality of light-emitting elements to send in timely spaced relationship fist pulsed light beams of different wavelength into a living human tissue supplied with blood, and directing second light beams that have passed through said tissue on to a light-receiving element so as to generate said multiplexed signal.

24. The method of claim 11, further comprising the steps of:

using a plurality of light-emitting elements to send in timely spaced relationship first pulsed light beams of different wavelength into a living human tissue supplied with blood, and directing second light beams that have passed through said tissue on to a light-receiving element so as to generate said multiplexed signal.

25. A method for deriving signals representing blood oxygen saturation comprising:

transmitting successive series of n pulses of light of different wavelengths at a given pulse repetition frequency;

producing electrical signals in response to the passage of said pulses of light through a body member or in response to their reflection from a body member;

applying the electrical signals to a noise-removing filter, expressing the signals at the output of the filter as a first matrix having a column of n elements;

multiplying said first matrix with a second matrix in $n^2$ form having coefficients representing the deviations in the modified signals produced by the filter;

the coefficients of said second matrix being selected such that they represent the values obtained by a matrix division of third and fourth matrices in $n^2$ form;

wherein the coefficients in the columns of said third matrix have been obtained, with the filter bypassed, from the responses to n pulse trains, each pulse train consisting of n pulses; and wherein the coefficients in the columns of said third matrix have been obtained, with the filter active, from the responses to n pulse trains, each pulse train consisting of n pulses.

26. The method of claim 25, wherein:

the principal diagonal coefficients of said second matrix have been decreased by unity;

the value of an m-th power of two has been factored out from the principal coefficients of said second matrix; and digitally multiplying said first matrix by said second matrix using digital words having a number of bits smaller than m.

27. The method of claim 25 wherein:

the principal diagonal coefficients of said second matrix have been standardized to unity;

the value of an m-th power of two has been factored out from the principal coefficients of said second matrix; and digitally multiplying said first matrix by said second matrix using digital words having a number of bits smaller than m.

28. The method of claim 25 wherein:

the principal diagonal coefficients of said second matrix have been standardized to unity;

said principal diagonal coefficients have further been decreased to unity;

the value of an m-th power of two has been factored out from the principal coefficients of said second matrix; and digitally multiplying said first matrix by said second matrix using digital words having a number of bits smaller than m.

29. The method of claim 25 wherein:

the principal diagonal coefficients of said second matrix have been standardized to unity;

an offset value has been multiplied with said second standardized matrix to generate a fifth column matrix with n elements of correction values; and subtracting said fifth column matrix from the product of said first and said second matrices.

* * * * *